United States Patent
Aizikovich

(10) Patent No.: US 11,472,785 B2
(45) Date of Patent: Oct. 18, 2022

(54) PROCESS FOR PURIFICATION OF TETRAHYDROCANNABINOLIC- AND CANNABIDIOLIC ACID FROM PLANT MATERIAL EXTRACT

(71) Applicant: AL&AM PHARMACHEM LTD., Rehovot (IL)

(72) Inventor: Alexander Aizikovich, Rehovot (IL)

(73) Assignee: AL&AM Pharmachem Ltd., Rehovot (IL)

(*) Notice: Subject to any disclaimer, the term of this patent is extended or adjusted under 35 U.S.C. 154(b) by 54 days.

(21) Appl. No.: 17/261,531

(22) PCT Filed: May 22, 2019

(86) PCT No.: PCT/IL2019/050578
§ 371 (c)(1),
(2) Date: Jan. 19, 2021

(87) PCT Pub. No.: WO2020/016875
PCT Pub. Date: Jan. 23, 2020

(65) Prior Publication Data
US 2021/0292295 A1    Sep. 23, 2021

Related U.S. Application Data

(60) Provisional application No. 62/700,413, filed on Jul. 19, 2018.

(51) Int. Cl.
*C07D 311/80* (2006.01)
*C07C 37/50* (2006.01)
*C07C 51/47* (2006.01)

(52) U.S. Cl.
CPC ............ *C07D 311/80* (2013.01); *C07C 37/50* (2013.01); *C07C 51/47* (2013.01)

(58) Field of Classification Search
CPC .................................................. C07D 311/89
USPC ......................................................... 549/390
See application file for complete search history.

(56) References Cited

U.S. PATENT DOCUMENTS

2015/0038567 A1    2/2015  Herkenroth et al.
2015/0203434 A1    7/2015  Flockhart et al.

FOREIGN PATENT DOCUMENTS

CA    2499492 A1    3/2005

OTHER PUBLICATIONS

Hung et al.; "Separation of cannabinoids on three different mixed mode colums containing carbon/nanodiamond/amine/polymer superficially porous particles". Journal of separation science. 38(17):pp. 2968-2974. (2015).
Huq et al.; Novel solid-phase extraction protocol for 11-nor-9-carboxy-?9- tetrahydrocannabinol from urine samples employing a polymeric mixed-mode cation-exchange resin, Strata-XC, suitable for gas chromatography—mass spectrometry or liquid chromatography—mass spectrometry analysis. Journal of Chromatography A, 1073 :pp. 355-361. (2005).
Stout et al.; "Solid-phase extraction and GC-MS analysis of THC-COOH method optimized for a high-throughput forensic drug-testing laboratory". Journal of analytical toxicology. 25(7):pp. 550-554. (2001).
International Search Report received in PCT Application No. PCT/IL2019/050578 dated Aug. 7, 2019.
Extended European search report dated Mar. 28, 2022 (5 pages) in the EP application No. 19837651.9.

*Primary Examiner* — Taofiq A Solola
(74) *Attorney, Agent, or Firm* — Knobbe, Martens, Olson & Bear, LLP

(57) ABSTRACT

The present invention relates to a highly economic process for the purification of a cannabinoid acid, more specifically THCA or CBDA, from either a crude cannabis plant material or a cell culture of said cannabis plant, using ion exchange resins. The purified cannabinoid acid obtained may then be decarboxylated to yield the corresponding cannabinoid, i.e., THC or CBD, respectively.

21 Claims, No Drawings

PROCESS FOR PURIFICATION OF TETRAHYDROCANNABINOLIC- AND CANNABIDIOLIC ACID FROM PLANT MATERIAL EXTRACT

TECHNICAL FIELD

The present invention relates to a process for purification of a cannabinoid acid, more specifically THCA or CBDA, from a crude cannabis plant extract. The purified cannabinoid acid obtained may then be decarboxylated to yield the corresponding cannabinoid, i.e., THC or CBD, respectively.

Abbreviations: ACN, acetonitrile; CBD, cannabidiol; CBDA, cannabinolic acid; CBN, cannabinol; DMF, dimethylformamide; HPLC, high performance liquid chromatography; LCMS, liquid chromatography-mass spectrometry; MTBE, methyl-tert-butyl ether; NMR, nuclear magnetic resonance; THC, $\Delta^9$-tetrahydrocannabinol; THCA, tetrahydrocannabinolic acid; THF, tetrahydrofuran; TLC, thin layer chromatography.

BACKGROUND ART

Marijuana is known as a natural drug useful in the treatment of inflammation, pain, psychoses, migraine and other disorders of the nervous system. Owing to their various activity, natural cannabinoids can often be used for the development of new potential drugs especially as starting materials for organic synthesis.

Cannabinoids are active ingredients of the *Cannabis sativa* plant, which mimic the effects of the endogenous cannabinoid system (endocannabinoids), and impact human body by activating cannabinoid receptors. Cannabinoid receptors include the cannabinoid type 1 (CB1) receptor, predominantly expressed in the brain, and the cannabinoid type 2 (CB2) receptor, primarily found in the immune system cells. Cannabinoids receptors as well as the entire endocannabinoid system are commonly treated as putative targets for the treatment of various diseases, including neurodegenerative diseases such as Parkinson's disease, Alzheimer's disease, and Huntington's disease; multiple sclerosis; and numerous inflammatory diseases such as asthma, allergic, Rheumatoid arthritis, and colitis.

Cannabinoids can be classified into endogenous cannabinoids; phytocannabinoids; and synthetic cannabinoids. Endocannabinoids are produced in the human body and mostly act as neuromodulators. They play an important role in inflammation, insulin sensitivity and metabolism, and have an important role in regulating the mood, appetite, pain sensation, inflammation response and memory. Phytocannabinoids naturally occur in the cannabis plant. There are about 100 cannabinoids in the cannabis plant. THC, CBD and CBN are the most widespread natural cannabinols. THC is the primary psychoactive component of the plant and has been used to treat a wide range of medical conditions. CBD is the most abundant non-psychoactive phytocannabinoid in the plant, and it is known to exert many positive pharmacological effects including anti-inflammatory, anti-anxiety, anti-diabetic, and anti-cancer effects. In addition, CBD is proposed to reverse some of the central side effects of THC, emphasizing the therapeutic value of the THC-CBD formulations.

Development of pharmacological cannabinoid applications is indeed strongly limited by psychotropic side effects mediated by the CB1 receptor ligands. For this reason, research is embracing development of the new strategies enabling isolation of individual cannabinoid compounds with peripherally restricted CB1 receptor activity. Such compounds can be dosed and standardized, enabling pharmaceutical activity without psychotropic side effects.

Cannabis extract obtained immediately from plant material contains up to about 70-75% cannabinoid acids together with terpenoids and other materials like lignin, gums, pigments and lecithin. Crude extracts from cannabis can be used immediately for patients suffering from many diseases, but they are not suitable for pharmacological purposes.

There are many publications disclosing the isolation and purification of THCA and CBDA, and the products obtained after decarboxylation thereof (WO2004016277, US2016228385, WO2013045115, WO2015070167, WO2016004410, WO2016127111). Some of these publications describe a technology for isolating said products without using chromatographic purification methods, which allows the production of cannabinoid acids on an industrial scale.

US2015038567 discloses a process for obtaining THCA salts without chromatographic separation. This process includes extraction of the plant material with a suitable solvent such as pentane or petroleum ether, extraction of the cannabinoid acids to a water phase with sodium- or potassium-hydroxide, and then re-extraction to an organic phase after addition of citric acid to water solution. The addition of amines such as dicyclohexylamine and cooling provided a residue of the cannabinoic acid salt with 95-97% purity.

WO2016179247 discloses a similar purification process that includes the extraction of cannabinoic acids from the plant material, adding an organic base to obtain their salts, washing with three solvents having different polarity, and acidification to obtain the pure acids.

US2017008870 discloses a method for obtaining a higher purity cannabinoid solvent extract from marijuana by a) performing a solvent extraction of the plant to yield a solvent extract; b) cooling the solvent extract; and c) removing the precipitate from the cooled solvent extract to yield a solvent extract filtrate, wherein the solvent extract filtrate has a higher purity of the at least one cannabinoid.

SUMMARY OF INVENTION

The present invention relates to a process for purification of cannabinoid acids, more specifically THCA and CBDA, by extraction of natural cannabinoid carboxylic acids from either a crude cannabis plant (e.g., *Cannabis saliva*) material or a cell culture of said cannabis plant, and subsequent treatment with a suitable ion exchange resin for isolation of said cannabinoid acids from said extract; treatment with an inorganic base to obtain said cannabinoid acids as suitable salts; and then treating said salts with an acid, e.g., using an acidic ion-exchange resin, so as to obtain said cannabinoid acids in chemically pure forms, i.e., with a purity higher than 90%, preferably higher than 92%, 93%, 94%, 95%, 96%, 97%, 98%, or 99%.

DETAILED DESCRIPTION OF THE PREFERRED EMBODIMENT

The present invention provides a process for purification of THCA or CBDA from a crude *cannabis* plant extract in an organic solvent, said process comprising the steps of:
  (i) passing said organic solvent containing said crude cannabis plant extract through a basic ion-exchange resin, thereby binding the THCA or CBDA present in said crude cannabis plant extract to said basic ion-exchange resin;

(ii) passing a strong base solution through said basic ion-exchange resin, thereby liberating the THCA or CBDA as a basic salt from said basic ion-exchange resin into said solution;

(iii) acidifying the solution obtained in step (ii) thereby neutralizing the THCA- or CBDA-basic salt to obtain THCA or CBDA, respectively;

(iv) extracting said THCA or CBDA with an organic solvent to obtain a solution of THCA or CBDA, respectively, in said solvent; and either:

(v) converting said THCA into a basic salt thereof, purifying said THCA salt to obtain a solid precipitate comprising said THCA salt, recrystallizing said precipitate to obtain said THCA salt in a chemically pure form, and converting said chemically pure THCA salt into said purified THCA; or (vi) drying the CBDA solution obtained, evaporating said solvent, and drying the material thus obtained under vacuum to obtain said purified CBDA.

The phrase "crude cannabis plant extract in an organic solvent" as used herein refers to any extract obtained by extracting either a crude cannabis plant, e.g., *Cannabis sativa*, material, or a cell culture of said cannabis plant, in an organic solvent. The organic solvent used for extracting said crude cannabis plant material or cell culture can be any suitable organic solvent such as, without being limited to, methanol, ethanol, isopropanol, hexanol, heptane, cyclohexane, methylcyclohexane, dichloromethane, acetonitrile, acetone, methyl ethyl ketone, diethyl ether, MTBE, chloroform, THF, dioxane, supercritical carbon dioxide (sCO$_2$) in an alcohol such as methanol, ethanol, or isopropanol, or a mixtures thereof. In certain embodiments, the organic solvent used for extracting said crude cannabis plant material or cell culture is an ammonia alcohol aqueous solution, obtained by mixing a pure alcohol, e.g., methanol, ethanol or isopropanol, with the corresponding amount of 10-25% of ammonia in water. Such an organic solvent enables better extraction of said cannabinoid acids from the plant material or cell culture and decreasing the content of nonpolar impurities such as terpenes and lignin.

The term "supercritical carbon dioxide" refers to a fluid state of carbon dioxide where it is held at or above its critical temperature (304.25 K, 31.10° C., 87.98° F.) and critical pressure (72.9 atm, 7.39 MPa, 1,071 psi), and thus has properties midway between a gas and a liquid.

According to step (i) of the process disclosed herein, the organic solvent containing the crude cannabis plant extract is passed through a basic ion-exchange resin so as to bind the THCA or CBDA present in said crude cannabis plant extract to said basic ion-exchange resin. The basic ion-exchange resin through which said organic solvent is passed can be any suitable basic ion-exchange resin such as those commercially available, and may be selected taking into consideration the specific organic solvent used for the extraction of said cannabis plant. In certain embodiments, said basic ion-exchange resin is a free base resin such as Amberlyst® A21 free base (Sigma-Aldrich), Amberlite® IRA-67 free base (Sigma-Aldrich), and Amberlite™ IRA67RF free base (Rohm and Haas). In particular such embodiments exemplified herein, the cannabis plant is extracted with cyclohexane or isopropanol so as to purify CBDA, or with ethanol so as to purify THCA, and the basic ion-exchange resin used is Amberlyst® A21 free base. After binding the THCA or CBDA present in the plant extract to the basic ion exchange resin, the resin is preferably washed with one or more suitable solvents to remove non-acid impurities such as terpenes.

The THCA and CBDA bound to said basic ion-exchange resin following step (i) of the process are of the formula A and B, respectively, wherein R$^+$ represents said ion exchange resin anion form. It should be noted that formula A represents the ionized form (COO$^-$) of both THCA and its isomer (6aR,10aR)-1-hydroxy-6,6,9-trimethyl-3-pentyl-6a,7,8,10a-tetrahydro-6H-benzo[c]chromene-4-carboxylic acid, referred to herein as "THCA 4-COOH" and considered as an impurity in the process.

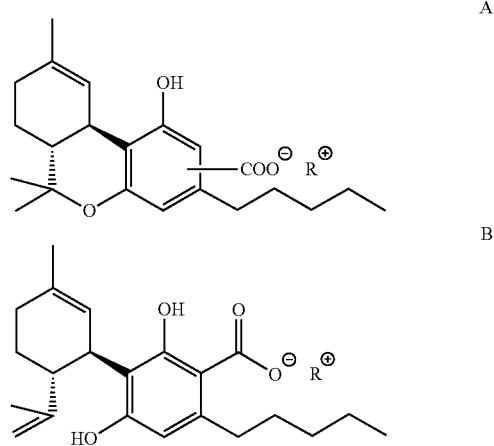

In step (ii) of the process disclosed herein, a strong base solution is passed through said basic ion-exchange resin so as to liberate, i.e., free or release, the THCA (including its THCA 4-COOH isomer) or CBDA bound to said basic ion-exchange resin, as a basic salt, into said solution. The base used to release the bound THCA or CBDA may be any strong base such as, without limiting, lithium hydroxide, sodium hydroxide, and potassium hydroxide. In particular embodiments, the strong base solution passed through the basic ion-exchange resin so as to liberate the THCA or CBDA bound to said resin is a sodium hydroxide solution. The THCA and CBDA salts obtained following step (ii) of the process are of the formula A and B, respectively, wherein R$^+$ represents, e.g., a metal ion such as lithium, sodium, or potassium ion.

According to the process of the present invention, the solution obtained in step (ii), which contains the THCA or CBDA as a basic salt, is acidified in step (iii) to thereby neutralize said basic salt and consequently obtain THCA or CBDA, respectively; and the THCA or CBDA is then extracted in step (iv) with an organic solvent to obtain a solution of THCA or CBDA, respectively, in said solvent. In certain embodiments, the solution obtained in step (ii) is acidified by passing through an acidic ion-exchange resin, e.g., Dowex® 50WX8 hydrogen form (Sigma-Aldrich), Amberlite™ IR120 H (Rohm and Haas), Ambejet™ 1000H (Rohm and Haas), and other strong acid resins in hydrogen form, and the THCA or CBDA thus obtained is then extracted by washing said acidic ion-exchange resin with said organic solvent to obtain a solution of THCA or CBDA, respectively, in said organic solvent.

Examples of suitable organic solvent that can be used for extracting said THCA or CBDA in step (iv) of the process disclosed herein include, without limiting, methanol, ethanol, isopropanol, hexanol, heptane, cyclohexane, methylcyclohexane, dichloromethane, acetonitrile, acetone, methyl ethyl ketone, diethyl ether, MTBE, chloroform, THF, dioxane, or a mixture thereof.

In certain embodiments, the invention provides a process for purification of THCA or CBDA from a crude cannabis plant extract in an organic solvent as described above, wherein (a) the basic ion-exchange resin through which the organic solvent containing said crude cannabis plant extract is passed in step (i) so as to bind the THCA or CBDA present in said plant extract to said basic ion-exchange resin is Amberlyst® A21 free base; (b) the strong base solution passed through said basic ion-exchange resin in step (ii) so as to liberate the THCA or CBDA bound to said resin is sodium hydroxide solution; (c) the solution obtained in step (ii), which contains the THCA or CBDA as a basic salt, is acidified by passing through an acidic ion-exchange resin such as Dowex® 50WX8 hydrogen form, to thereby neutralize said basic salt and consequently obtain THCA or CBDA, respectively; and (d) the THCA or CBDA obtained is then extracted by washing said acidic ion-exchange resin with said organic solvent to obtain a solution of THCA or CBDA, respectively, in said organic solvent.

Steps (v) and (vi) of the process of the present invention represent two alternatives aimed at purifying the THCA or CBDA, respectively, from their organic solution obtained in step (iv).

The THCA solution obtained in step (iv) further comprises the isomer THCA 4-COOH. Isolation and purification of the THCA from the isomer mixture is carried out as described in step (v), based on the different solubilities of the two isomers in organic solvents, by converting said isomers into basic salts thereof; purifying said salts to obtain a solid precipitate comprising said salts; recrystallizing said precipitate to obtain the THCA salt in a chemically pure form; and converting said chemically pure THCA salt into said purified THCA.

In certain embodiments, the present invention provides a process for purification of THCA from a crude cannabis plant extract in an organic solvent as defined in any one of the embodiments above, wherein the THCA obtained in step (iv) is converted to the ammonium salt thereof; said THCA salt is purified by dissolving in an organic solvent, e.g., heptane, to obtain said solid precipitate comprising said THCA ammonium salt; said THCA ammonium salt is recrystallized from an organic solvent, e.g., a mixture of MTBE and heptane, to obtain said THCA ammonium salt in a chemically pure form, which is then dried; and said dried chemically pure THCA ammonium salt is converted into said purified THCA by dissolving in an organic solvent, e.g., MTBE, washing the organic solution obtained with acidic water, e.g., with citric acid in water, and separating the organic phase.

The conversion of the THCA obtained in step (iv) to the ammonium salt thereof provides ammonium salts of both THCA and THCA 4-COOH; however, the solubility of THCA 4-COOH ammonium salt in hydrocarbons is substantially better than that of THCA, and while the latter precipitate from the organic solvent in which said salts are dissolved, the former remains in the solution and can thus be removed. The THCA ammonium salt is then recrystallized from an organic solvent to obtain the THCA salt in a chemically pure form, which can then be reacted with suitable acids, e.g., mineral acids, acetic acid, citric acid, and ion exchange resin (cation form) to obtain THCA with purity of at least 90%, 92%, 94%, 95%, 96%, 97%, 98%, or 99%.

According to the alternative step (vi), the CBDA organic solution obtained is first dried so as to remove water residues, and the dried organic solvent is then evaporated to obtain a material that is dried under vacuum to obtain CBDA with purity of at least 90%, 92%, 94%, 95%, 96%, 97%, 98%, or 99%.

In certain embodiments, the present invention provides a process for purification of CBDA from a crude cannabis plant extract in an organic solvent as defined in any one of the embodiments above, wherein the CBDA solution obtained in step (iv) is first dried over anhydrous magnesium sulfate, sodium sulfate, or calcium chloride, and the dried organic solvent is then evaporated to obtain a material that is dried under vacuum to obtain purified CBDA.

The purified THCA and CBDA obtained by the process disclosed herein may be decarboxylated to obtain purified THC and CBD, respectively. In certain embodiments, the process of the present invention, as defined in any one of the embodiments above, thus further comprises the step of decarboxylation of the purified THCA or CBDA obtained in step (v) or (vi) to obtain purified THC or CBD, respectively.

According to the present invention, THC may further be obtained directly from the THCA salt obtained as an intermediate during step (v) of the process disclosed herein. In certain embodiments, the dried chemically pure THCA salt obtained in step (v) is decarboxylated by dissolving said THCA salt in an organic solvent; heating the solution thus obtained under pressure higher than ambient pressure, more specifically under pressure created by vapours of said organic solvent so as to prevent oxidation of THC, to thereby obtain THC in said organic solvent; and removing said organic solvent to obtain said purified THC. In particular such embodiments, the THCA obtained in step (iv) is converted in step (v) to the ammonium salt thereof, and THC is obtained as described hereinabove starting from the dried chemically pure THCA ammonium salt. Alternatively, THC may be obtained by the same procedure starting from the solid precipitate that comprises the ammonium salts of both THCA isomers rather than from the dried chemically pure THCA ammonium salt.

Similarly, the dried chemically pure CBDA obtained in step (vi) may be decarboxylated to obtain CBD, by dissolving said purified CBDA in an organic ammonia-containing solution to thereby obtain CBDA ammonium salt; heating the solution thus obtained under pressure higher than ambient pressure, more specifically under pressure created by vapours of said organic solvent so as to prevent oxidation of CBD, to thereby obtain CBD in said organic solvent; removing said organic solvent; and recrystallizing said CBD to obtain said purified CBD.

Non-limiting examples of organic solvents that may be used in the decarboxylation step, so as to dissolve the purified THCA or CBDA obtained in step (v) or (vi), respectively, include methanol, ethanol, isopropanol, hexanol, heptane, cyclohexane, methylcyclohexane, dichloromethane, acetonitrile, acetone, methyl ethyl ketone, diethyl ether, MTBE, chloroform, THF, dioxane, or a mixture thereof.

In sharp contrast to the teaching of the prior art, the process disclosed herein is the first one using ion exchange resins for selective isolation of cannabinoid acids from an organic extract of a crude cannabis plant material or a cell culture of said cannabis plant, by separate absorption-desorption processes. This process enables obtaining the desired cannabinoid acid, i.e., THCA or CBDA, with very high purity, and it is highly economic process, as the it allows multiple using of the resins.

The invention will now be illustrated by the following non-limiting Examples.

EXAMPLES

Materials and Methods

Isolation and purification procedures were provided in appropriate solvents such as water, methanol, ethanol, solvents immiscible with water, or solvent miscible with water such as hydrocarbons with up to 30 carbon atoms, halogenated hydrocarbons with up to 20 carbon atoms, e.g., dichloromethane or chloroform, ethers such as 2-methyl-tetra-hydrofuran, alcohols, carboxylic acids with up to 16 carbon atoms, amides with up to 20 carbon atoms, esters with up to 60 carbon atoms, carbon dioxide, sulfur dioxide, ammonium solution in water and in alcohols, water with a phase transfer catalyst, the acidic catalysts themselves, cyclohexane, MTBE, THF, CAN, DMF, and mixtures of the aforesaid. The completion of the isolation and purification procedures was monitored by TLC, the level of purity was examined by HPLC and LCMS. All products were characterized by mass and NMR spectroscopy by 400 MHz (VARIAN). These methods were consisted with assigned structures.

Example 1. Preparation of THCA (Both 2-COOH and 4-COOH)

As depicted in Scheme 1, dry plant material *Cannabis sativa* (10 g) was extracted with cyclohexane (150 ml) for one hour under $N_2$ to prevent oxidation and filtrated. The solid was washed twice with 50 ml cyclohexane, and all solvents together were added to anion exchange resin Amberlyst® A21 (free base 3) and stirred for an hour. The degree of acid uptake was monitored by TLC. The resin was filtrated and washed twice with ethanol to remove cyclohexane traces (after distillation cyclohexane may be re-used). The resin was then added to a solution of NaOH (1.2 g, 30 mmol) in 150 ml 95% ethanol and the mixture was stirred for two hours. The resin was filtrated and washed twice with 50 ml ethanol (resin may be re-used). By HPLC, the solution contained Na-salts of THCA (2-COOH) and THCA (4-COOH) in amounts of 91% and 5%, respectively. All the solutions were added to ion exchange resin Dowex® 50WX8 (hydrogen form) and stirred for 30 min. The resin was filtrated and washed twice with 50 ml ethanol.

Example 2. Preparation of THCA (2-COOH) with Purity of >97%

As depicted in Scheme 2, to an ethanol solution of the THCA obtained in Example 1 (a mixture of 2-COOH and 4-COOH), 20 ml of 32% ammonia was added and the solvent was evaporated till oily residue was obtained. The product was dried in deep vacuum for 24 hours, then 150 ml heptane was added, and the mixture was stirred until white precipitate was obtained. After filtration, solid was recrystallized from MTBE-heptane and dried under vacuum. The yield of THCA (2-COOH) ammonium salt was 620 mg. Purity >97%. $^1$H NMR ($CD_3OD$), δ: 0.88-0.91 (3H, t, CH); 1.06 (3H, s, CH); 1.31-1.43 (9H, m, CH); 1.51-1.55 (3H, m, CH); 1.57 (3H, s, CH); 1.65-1.90 (1H, m, CH); 2.13-2.14 (2H, m, CH); 2.51-2.59 (2H, m, CH); 2.92-3.17 (1H, d, CH); 3.31-3.32 (3H, d, CH); 6.03 (1H, s, CH); 6.47 (1H, s, CH). $^{13}$C NMR ($CD_3OD$), δ: 14.51, 19.54, 23.55, 23.72, 26.27, 27.90, 32.29, 32.81, 33.35, 35.11, 36.64, 47.48, 78.49, 110.11, 110.70, 111.27; 126.06, 133.44, 146.71, 157.20, 165.58; 176.80. Molecular ion observed $[M-H]^+=359$ consistent with the molecular formula $C_{22}H_{30}O_4$.

The THCA (2-COOH) ammonium salt obtained was dissolved in MTBE and washed with a solution of citric acid in water. The organic phase was separated and dried over sodium sulfate. After removing off solvent, 585 mg of THCA (2-COOH) with purity higher than 97% was obtained. $^1$H NMR ($CD_3OD$), δ: 0.89-0.92 (3H, t, CH); 1.07 (3H, s, CH); 1.29-1.37 (5H, m, CH); 1.41 (3H, s, CH); 1.51-1.61 (3H, m, CH); 1.66 (3H, s, CH); 1.95-1.97 (1H, m, CH); 2.15-2.17 (2H, m, CH); 2.77-2.92 (2H, m, CH); 3.16-3.17 (1H, d, CH); 3.31-3.32 (3H, d, CH); 6.14 (1H, s, CH); 6.39 (1H, s, CH). $^{13}$C NMR ($CD_3OD$), δ: 14.43, 19.64, 23.54, 26.17, 27.79, 32.22, 32.83, 33.22, 34.87, 37.52, 47.21, 79.34, 104.58, 110.83, 112.97, 125.29; 134.05, 147.16, 160.79, 165.37; 176.58. Molecular ion observed $[M-H]^+=359$ consistent with the molecular formula $C_{22}H_{30}O_4$.

Example 3. Preparation of THCA (Mixture of 2-COOH and 4-COOH)

Dry plant material *Cannabis sativa* (10 g) was extracted with i-propanol (200 ml) containing 20 ml 25% solution of ammonia for one hour under $N_2$ to prevent oxidation and filtrated. The solid was washed twice with 50 ml i-propanol, and all the solvents together were added to anion exchange resin Amberlyst® A21 (free base 3) and stirred for an hour. The degree of acid uptake was monitored by TLC. The resin was filtrated and washed twice with i-propanol to remove traces of ammonia solution (after distillation i-propanol may be re-used). Then resin was added to a solution of KOH (1.2 g, 20 mmol) in 100 ml i-propanol and the mixture was stirred for two hours. The resin was filtrated and washed twice with 50 ml of i-propanol (resin may be re-used).

All the solutions were added to ion exchange resin Dowex® 50WX8 (hydrogen form) and stirred for 30 min. The resin was filtrated and washed twice with 50 ml i-propanol. The solvent was evaporated, and the crude product was dried in vacuum. By HPLC, white solid contained THCA (a mixture of 2-COOH and 4-COOH) in amounts of 91% and 6%, respectively. Molecular ion observed $[M-H]^+=359$ consistent with the molecular formula $C_{22}H_{30}O_4$.

Example 4. Preparation of THC

As depicted in Scheme 3, THCA (a mixture of 2-COOH and 4-COOH) ammonium salts (20 mg, 0.05 mmol) was heated in i-propanol in a sealed tube at a temperature of 120-125° C. in the dark for three hours. After cooling, the crude solution was stirred with ion exchange resin Amberlyst® IRA-67 (weakly base) to remove unreacted THCA. After filtration of resin solvent was evaporated and THC was obtained. Yield 96% (14 mg, 0.045 mmol). Molecular ion observed $[M-H]^+=315$ consistent with the molecular formula $C_{21}H_{30}O_2$.

Example 5. Preparation of CBDA with Purity >90%

Dry technical hemp (10 g) was extracted with ethanol (200 ml) containing 20 ml 25% solution of ammonia for one hour under $N_2$ to prevent oxidation and filtrated. The solid was washed twice with 50 ml ethanol. All the solvents together were added, stirred with 0.5 g of activated carbon, stirred for 30 min under $N_2$, and filtrated. The filtrate was added to anion exchange resin Amberlyst® A21 (free base)

and stirred for an hour. The degree of acid uptake was monitored by TLC. The resin was filtrated and washed twice with ethanol to remove traces of ammonia solution (after distillation ethanol may be re-used). Then resin was added to a solution of NaOH (1.2 g, 30 mmol) in 100 ml ethanol and the mixture was stirred for two hours. The resin was filtrated and washed twice with 50 ml of ethanol (resin mat be re-used). To the solution of CBDA sodium salt, 100 ml water was added, and the mixture was extracted twice with pentane. The water phase was separated, a solution of 100 ml of 0.5M citric acid was added, and the mixture was extracted with MTBE. The organic phase was dried over sodium sulfate, the solvent was evaporated, and the crude oil was dried under deep vacuum for 24 hours. By HPLC, CBDA had purity 93%. Molecular ion observed [M-H]$^+$=359 consistent with the molecular formula $C_{22}H_{30}O_4$.

Example 6. Preparation of CBD with Purity >98%

As depicted in Scheme 4, dry technical hemp (10 g) was extracted with ethanol (200 ml) containing 20 ml 25% solution of ammonia for one hour under $N_2$ to prevent oxidation and filtrated. The solid was washed twice with 50 ml ethanol. All the solvents together were added stirred with 0.5 g of activated carbon, stirred for 30 min under $N_2$, and filtrated. The filtrate was added to a column equipped with 25 g anion exchange resin Amberlyst® A21 (free base) and filtrated through column under. The degree of acid uptake was monitored by TLC. The resin was washed twice with ethanol to remove traces of ammonia solution (after distillation ethanol may be re-used). Then column was washed with a solution of NaOH (1.2 g, 30 mmol) in 200 ml ethanol solution of NaOH (1.2 g, 30 mmol) in 100 ml ethanol. The degree of sodium salt extraction was monitored by HPLC. After removing all amount of salt, the column may be re-used. To the solution of CBDA sodium salt, 100 ml of water was added, and the mixture was extracted twice with pentane. The water phase was separated, a solution of 100 ml of 0.5M citric acid was added, and the mixture was extracted with MTBE. The organic phase was dried over sodium sulfate, the solvent was evaporated, and crude oil was dried under deep vacuum for 24 hours. By HPLC, CBDA had purity 91.5%. Molecular ion observed [M-H]$^+$=359 consistent with the molecular formula $C_{22}H_{30}O_4$.

CBDA was dissolved in 20 ml i-propanol solution containing 2 ml 25% ammonia and was heated in sealed tube at a temperature of 120-125° C. in the dark for two hours. After cooling, crude solution was diluted with 50 ml of water, extracted with heptane, and dried over sodium sulfate. The heptane was evaporated, and CBD was crystallized from pentane. Yield 550 mg. Molecular ion observed [M-H]$^+$=315 consistent with the molecular formula $C_{21}H_{30}O_2$.

APPENDIX

Scheme 1

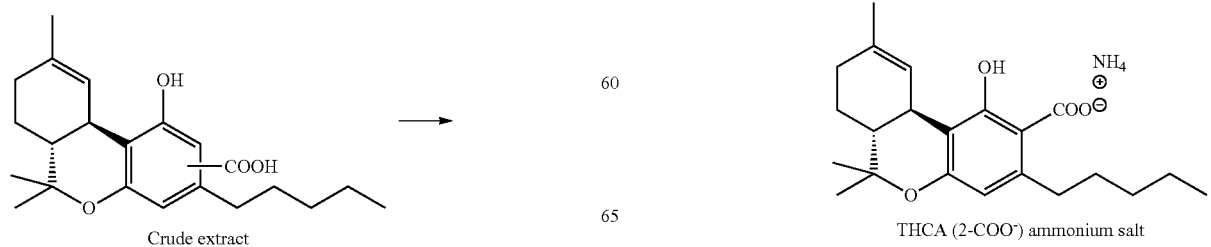

Crude extract

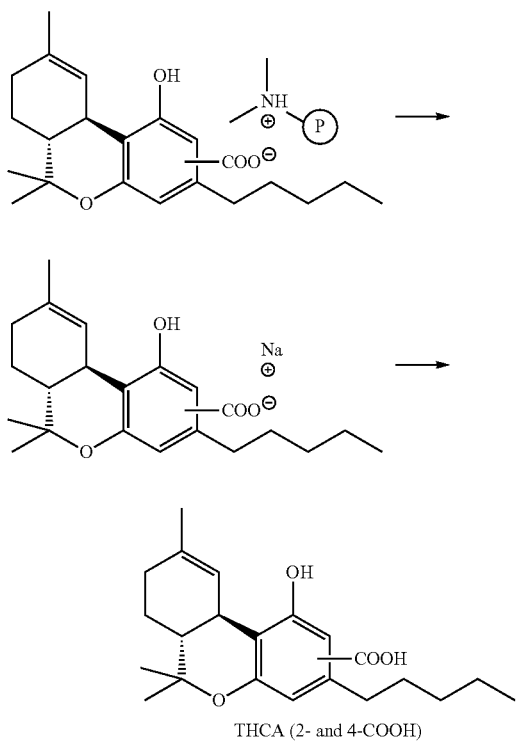

Scheme 2

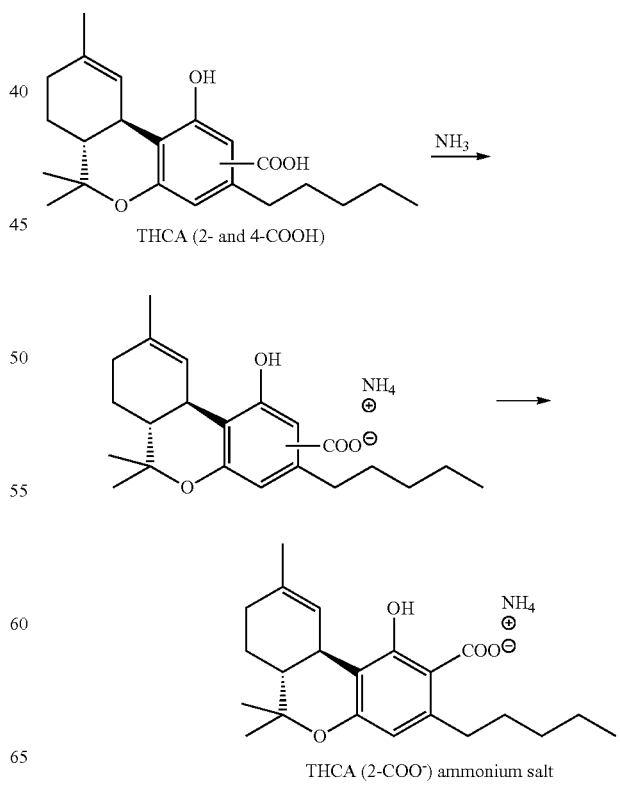

Scheme 3

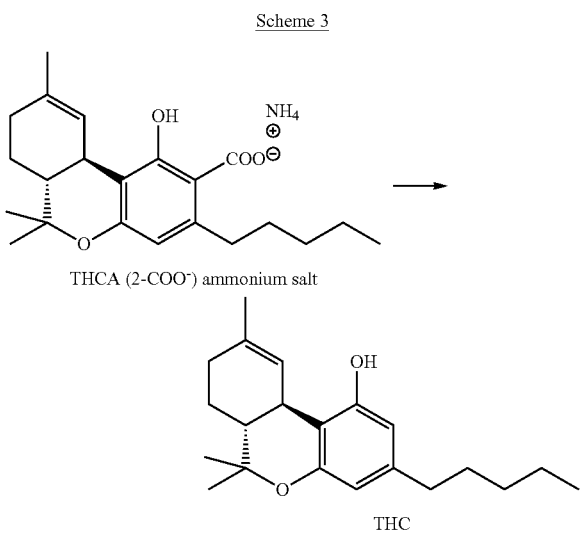

THCA (2-COO⁻) ammonium salt

THC

Scheme 4

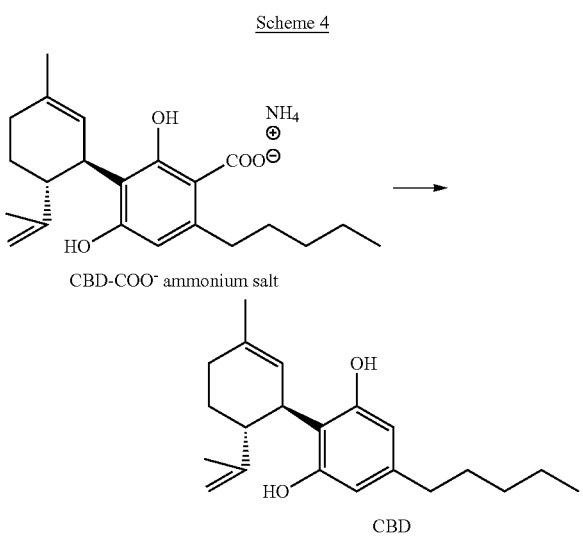

CBD-COO⁻ ammonium salt

CBD

What is claimed is:

1. A process for purification of tetrahydrocannabinolic acid (THCA) or cannabidiolic acid (CBDA) from a crude cannabis plant extract in an organic solvent, said process comprising:
   (i) passing said organic solvent containing said crude cannabis plant extract through a basic ion-exchange resin, thereby binding the THCA or CBDA present in said crude cannabis plant extract to said basic ion-exchange resin;
   (ii) passing a strong base solution through said basic ion-exchange resin, thereby liberating the THCA or CBDA as a basic salt from said basic ion-exchange resin into said solution;
   (iii) acidifying the solution obtained in said (ii) thereby neutralizing the THCA- or CBDA-basic salt to obtain THCA or CBDA, respectively;
   (iv) extracting said THCA or CBDA with an organic solvent to obtain a solution of THCA or CBDA, respectively, in said solvent; and
   either:
   (v) converting said THCA into a basic salt thereof, purifying said THCA salt to obtain a solid precipitate comprising said THCA salt, recrystallizing said precipitate to obtain said THCA salt in a chemically pure form, and converting said chemically pure THCA salt into said purified THCA; or
   (vi) drying the CBDA solution obtained, evaporating said solvent, and drying the material thus obtained under vacuum to obtain said purified CBDA.

2. The process of claim 1, wherein said cannabis plant is *Cannabis sativa*.

3. The process of claim 1, wherein said organic solvent containing said crude cannabis plant extract is methanol, ethanol, isopropanol, hexanol, heptane, cyclohexane, methylcyclohexane, dichloromethane, acetonitrile, acetone, methyl ethyl ketone, diethyl ether, methyl-tert-butyl ether (MTBE), chloroform, tetrahydrofuran (THF), dioxane, supercritical $CO_2$ in an alcohol.

4. The process of claim 1, wherein said basic ion-exchange resin is a free base resin.

5. The process of claim 1, wherein said strong base used in said (ii) is lithium hydroxide, sodium hydroxide, or potassium hydroxide.

6. The process of claim 1, wherein said (iii) is carried out by passing the solution obtained in said (ii) through an acidic ion-exchange resin; and said (iv) is carried out by washing said acidic ion-exchange resin with said organic solvent.

7. The process of claim 6, wherein said acidic ion-exchange resin is an acidic-exchange resin in hydrogen form.

8. The process of claim 1, wherein said organic solvent used in said (iv) is methanol, ethanol, isopropanol, hexanol, heptane, cyclohexane, methylcyclohexane, dichloromethane, acetonitrile, acetone, methyl ethyl ketone, diethyl ether, MTBE, chloroform, THF, dioxane, or a mixture thereof.

9. The process of claim 1, wherein
   (a) said basic ion-exchange resin through which said organic solvent containing said crude cannabis plant extract is passed in said (i) is a free base resin;
   (b) said strong base solution passed through said basic ion-exchange resin in said (ii) is sodium hydroxide;
   (c) said (iii) is carried out by passing the solution obtained in said (ii) through an acidic ion-exchange resin; and
   (d) said (iv) is carried out by washing said acidic ion-exchange resin with said organic solvent.

10. The process of claim 1, for purification of THCA from said crude cannabis plant extract in said organic solvent, wherein the THCA obtained in said (iv) is converted to the ammonium salt thereof; said THCA ammonium salt is purified by dissolving in an organic solvent to obtain said solid precipitate comprising said THCA ammonium salt; said THCA ammonium salt is recrystallized from an organic solvent to obtain said THCA ammonium salt in a chemically pure form, which is then dried; and said dried chemically pure THCA ammonium salt is converted into said purified THCA by dissolving in an organic solvent, washing the organic solution obtained with acidic water, and separating the organic phase.

11. The process of claim 1, for purification of CBDA from said crude cannabis plant extract in said organic solvent, wherein the CBDA solution obtained in said (iv) is dried over anhydrous magnesium sulfate, sodium sulfate, or calcium chloride.

12. The process of claim 1, further comprising decarboxylation of said purified THCA or CBDA to obtain purified THC or CBD, respectively.

13. The process of claim 10, wherein said dried chemically pure THCA ammonium salt is decarboxylated by dissolving said THCA ammonium salt in an organic solvent;

heating the solution obtained under pressure higher than ambient pressure to thereby obtain THC in said organic solvent; and removing said organic solvent to obtain purified THC.

14. The process of claim 11, wherein said dried purified CBDA is decarboxylated by dissolving said purified CBDA in an organic solution containing ammonia to thereby obtain CBDA ammonium salt in said solution; heating the solution obtained under pressure higher than ambient pressure to thereby obtain CBD in said organic solvent; removing said organic solvent; and recrystallizing said CBD to obtain purified CBD.

15. The process of claim 13, wherein said organic solvent is methanol, ethanol, isopropanol, hexanol, heptane, cyclohexane, methylcyclohexane, dichloromethane, acetonitrile, acetone, methyl ethyl ketone, diethyl ether, MTBE, chloroform, THF, dioxane, or a mixture thereof.

16. The process of claim 14, wherein said organic solvent is methanol, ethanol, isopropanol, hexanol, heptane, cyclohexane, methylcyclohexane, dichloromethane, acetonitrile, acetone, methyl ethyl ketone, diethyl ether, MTBE, chloroform, THF, dioxane, or a mixture thereof.

17. The process of claim 3, wherein said organic solvent containing said crude cannabis plant extract is supercritical $CO_2$ in an alcohol selected from the group consisting of methanol, ethanol, isopropanol, and a mixture thereof.

18. The process of claim 9, wherein said (iii) is carried out by passing the solution obtained in said (ii) through an acidic ion-exchange resin hydrogen form.

19. The process of claim 10, wherein said THCA ammonium salt is purified by dissolving in heptane to obtain said solid precipitate comprising said THCA ammonium salt.

20. The process of claim 10, wherein said THCA ammonium salt is recrystallized from an MTBE-heptane mixture to obtain said THCA ammonium salt in a chemically pure form.

21. The process of claim 10, wherein said chemically pure THCA ammonium salt is purified by converted into said purified THCA by dissolving in MTBE.

* * * * *